United States Patent
Lambert et al.

(10) Patent No.: US 6,229,009 B1
(45) Date of Patent: May 8, 2001

(54) POLYCARBOXYLIC BASED CROSS-LINKED COPOLYMERS

(75) Inventors: Nada Lambert, Paris; Denis Labarre, Villebon sur Yvette; Hatem Fessi, Lyons, all of (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/242,587

(22) PCT Filed: Aug. 29, 1997

(86) PCT No.: PCT/FR97/01534

§ 371 Date: Feb. 18, 1999

§ 102(e) Date: Feb. 18, 1999

(87) PCT Pub. No.: WO98/08897

PCT Pub. Date: Mar. 5, 1998

(51) Int. Cl.[7] .......................... C08B 37/08; C08B 37/10; C08B 37/00
(52) U.S. Cl. .......................... 536/123.1; 525/54.1; 536/2; 536/20; 536/21; 536/80; 536/88; 536/106; 536/119; 424/488
(58) Field of Search .......................... 525/54.1; 424/488; 536/20, 21, 2, 80, 88, 106, 119, 123.1

(56) References Cited

U.S. PATENT DOCUMENTS

| | | | |
|---|---|---|---|
| 4,026,851 | 5/1977 | Greene | 260/23 |
| 4,330,440 | * 5/1982 | Ayers et al. | 525/54.31 |
| 5,017,229 | 5/1991 | Burns et al. | 106/162 |
| 5,439,983 | * 8/1995 | Ahmed et al. | 525/296 |
| 5,498,705 | * 3/1996 | Oin | 536/20 |
| 5,550,189 | * 8/1996 | Qin et al. | 525/54.3 |
| 5,616,568 | * 4/1997 | Pouyani et al. | 514/54 |
| 5,690,961 | * 11/1997 | Nguyen | 424/488 |
| 5,874,417 | * 2/1999 | Prestwich et al. | 514/54 |
| 5,874,500 | * 2/1999 | Rhee et al. | 525/54.1 |

FOREIGN PATENT DOCUMENTS

| | | |
|---|---|---|
| 0334167 | 9/1989 | (EP) . |
| 57-065328 | * 4/1982 | (JP) . |
| 61-094655 | * 5/1986 | (JP) . |
| 8902445 | 3/1989 | (WO) . |
| 9116881 | 11/1991 | (WO) . |

OTHER PUBLICATIONS

Bauer et al., "Review about Novel Pharmaceutical Excipients for Colon–Targeting", Drugs Made in Germany, vol. 35(3): 85–89, 1992.*

Dumitriu et al. "Hydrogels Based on Polysaccharides", chapter 6 of Polysaccharides in Medicinal Applications, edited by Severian Dumitriu, publ. by. Marcel Dekker, Inc. 1996*

* cited by examiner

Primary Examiner—Howard C. Lee
(74) Attorney, Agent, or Firm—Bierman, Muserlian and Lucas

(57) ABSTRACT

A cross-linked copolymer based on at least one non-crosslinked polycarboxylic polysaccharide and at least one second non-crosslinked polycarboxylic polymer which is not a polycarboxylic polysaccharide and a cross-linking agent having at least two amine functions.

21 Claims, 1 Drawing Sheet

POLYCARBOXYLIC BASED CROSS-LINKED COPOLYMERS

This application is a 371 of PCT/FR97/01534 filed Aug. 29, 1997.

The invention relates to cross-linked copolymers based on non cross-linked polycarboxylic polymers, said copolymers containing at least one polycarboxylic polysaccharide. The invention also relates to a process for the preparation of these copolymers and their use in particular as a support in pharmaceutical compositions.

Certain compounds with a polymeric structure containing a polycarboxylic polysaccharide, optionally modified, have been described in the literature. For example, Patent Application WO89/02445 describes a gel based on hyaluronic acid; but, in its structure, this gel only comprises hyaluronic acid and no other polycarboxylic polymer. Moreover, no cross-linking agent is used in the preparation of this gel. The compound obtained in this way is mainly used in surgery. Patent Application WO91/16881 describes, among others, the combination of an active ingredient with a matrix constituted by a modified polymer, i.e. to which saccharides are grafted. This modified polymer can be a natural polymer such as chondroitin sulphate. However, this matrix contains only one type of polymer.

The copolymers according to the invention based on polycarboxylic polymers contain at least one polycarboxylic polysaccharide and at least one other polycarboxyclic polymer which is not a polysaccharide. The combination of a polysaccharide with another type of polycarboxylic polymer allows the modulation of the properties of the polysaccharides such as the hydrophilicity. In this way, copolymers can be obtained with appropriate degradation properties according to their uses. Moreover, the copolymers according to the invention are advantageously prepared in an aqueous medium. This is a real advantage as it is almost impossible to totally eliminate the solvents in a polymer structure: the existence of traces of residual aqueous solvents is generally more easily acceptable and accepted than traces of residual organic solvents such as dimethylsulphoxide or dimethylformamide.

A subject of the invention is cross-linked copolymers based on non cross-linked polycarboxylic polymers and a cross-linking agent comprising at least two amine functions, said copolymers comprising at least one polycarboxylic polysaccharide and at least one other non cross-linked polycarboxylic polymer which is not a polycarboxylic polysaccharide.

The non cross-linked polycarboxylic polysaccharides can be chosen, for example, from glycosaminoglycans, pectinic acid, alginic acid, carboxylic derivatives of dextran such as carboxymethyldextrans, or the carboxylic derivatives of cellulose such as carboxymethylcelluloses. Among the glycosaminoglycans, there can be mentioned hyaluronic acid, chondroitin sulphate, heparin, dermatan sulphate, heparan sulphate, keratan sulphate or a mixture of the latter. Among the polycarboxylic polymers which are not polysaccharides, there can be mentioned poly(glutamic acid), poly(aspartic acid), poly(maleic acid), poly(malic acid) or poly(fumaric acid), the polycarboxylic acrylic polymers such as poly(acrylic acid), poly(methacrylic acid) or the copolymers of the latter such as the Eudragits® L and S. The expression polycarboxylic polymers includes polymers as defined above but also the partly or totally substituted derivatives of these polymers such as, for example, their esters, their amides or their salts, copolymers containing the units present in these polycarboxylic polymers or in their derivatives as defined above, but also a mixture of these polymers and/or their derivatives and/or their copolymers as defined above.

A more particular subject of the invention is cross-linked copolymers as defined above, characterized in that the polysaccharide is chosen from pectinic or alginic acid, glycosaminoglycans, and preferably hyaluronic acid, chondroitin sulphate, heparin, dermatan sulphate, heparan sulphate, keratan sulphate or a mixture of the latter.

A more particular subject of the invention is cross-linked copolymers as defined above, characterized in that the non cross-linked polycarboxylic polymer which is not a polycarboxylic polysaccharide is chosen from polycarboxylic acrylic polymers, poly(glutamic acid), poly(aspartic acid), poly(maleic acid), poly(malic acid) or poly(fumaric acid). The non cross-linked polycarboxylic polymer which is not a polycarboxylic polysaccharide is preferably a polycarboxylic acrylic polymer and more particularly poly(acrylic acid) or poly(methacrylic acid).

The polycarboxylic polymers according to the invention are linked together by a cross-linking agent. This cross-linking agent comprises at least two amine functions which are capable of reacting with the free carboxylic functions of said non cross-linked carboxylic polymers. It can be chosen, for example, from proteins, polyamines, triamines, diamines, natural or synthetic amino acids, or the derivatives of compounds as defined above such as, for example, their salts, esters or amides. Among the amino acids there can be mentioned, for example, arginine, lysine, histidine and ornithine. Among the diamines there can be mentioned ethylenediamine, butanediamine, hexanediamine, heptanediamine, octanediamine or dodecanediamine. Among the polyamines there can be mentioned chitosan, poly(amino acids) such as polylysine or polyornithine, as well as the copolymers of these polyamines. The cross-linking agent can also be chosen from compounds such as spermine, spermidine, melamine, guanidine or diethylenetriamine. The cross-linking agent used is preferably an amino acid and advantageously lysine, ornithine or histidine.

A more particular subject of the invention is also cross-linked copolymers as defined above, characterized in that the polycarboxylic polysaccharide is a polycarboxylic polysaccharide which can be degraded by the microbial flora of the colon such as chondroitin sulphate, hyaluronic acid, pectinic acid or heparin.

A more particular subject of the invention is cross-linked copolymers as defined above, characterized in that the polycarboxylic polysaccharide is chondroitin sulphate and the other said polcarboxylic polymer is chosen from poly (acrylic acid) and poly(methacrylic acid), and the cross-linking agent is lysine or histidine.

A subject of the invention is also a process for the preparation of cross-linked copolymers as defined above, said process characterized in that said non cross-linked polycarboxylic polymers constituting the cross-linked copolymer are reacted in the presence of an activator and a cross-linking agent comprising at least two amine functions, in an appropriate reaction medium. The preparation of cross-linked copolymers as defined above is preferably carried out in an aqueous medium. The expression aqueous medium means a medium only containing water or water mixed with one or more solvents which are miscible with water such as, for example, acetone or lower alcohols such as ethanol. The aqueous medium preferably only comprises water. The implementation of the process according to the invention can be carried out in various manners. In fact, the process may consist in mixing non cross-linked polycarboxylic polymers and the cross-linking agent, then adding the activator. The cross-linking process according to the invention can also consist in mixing together non cross-linked polycarboxylic polymers and the activator, then adding the cross-linking agent. The process may also consist in cross-linking one of the non cross-linked polycarboxylic polymers constituting the copolymer, mixing said polymer with the cross-linking agent then the activator, or with the activator then the cross-linking agent, then adding at least one other non cross-linked polycarboxylic polymer to the reaction medium, in order to cross-link it with said polymer present in the reaction mixture. During the implementation of the process, the reagents introduced can previously be solubilized in the chosen reaction medium. The non cross-linked polycarboxylic polymers and the cross-linking agent are preferably mixed together in an aqueous medium until solubilization then the activator is added. The process is implemented at a temperature comprised between −30 and 100° C., preferably between 0 and 40° C. and most preferably at ambient temperature. The implementation temperature for the cross-linking process is of course lower than the degradation or decomposition temperatures of the reagents introduced.

The relative proportions of the reagents constituted by the non cross-linked polycarboxylic polymers, the cross-linking agent and the activator can vary according to the characteristics of the sought copolymers. The proportions of the non cross-linked polycarboxylic polymers are defined with respect to the molar quantities of the carboxylic functions present per base unit. The non cross-linked polycarboxylic polymers can vary within a molar ratio comprised between 0.01 and 100. The molar ratio of the cross-linking agent with respect to the total carboxylic functions can vary from 0.01 to 100. The molar ratio of the activator with respect to the total carboxylic functions can vary from 0.01 to 100.

The activator can be chosen from coupling agents in standard use in peptide synthesis. The activator can thus be chosen, for example, from carbodiimides, quinoline derivatives or mixed anhydrides. As examples of carbodiimides, there can be mentioned hydrohalides such as N-(3-dimethylaminopropyl)-N'-ethyl carbodiimide hydrochloride (EDC), N-cyclohexyl-N'-(2-morpholinoethyl) carbodiimide (CMC). As examples of quinoline derivatives, there can be mentioned 2-ethoxy-N-ethoxycarbonyl-1,2-dihydroquinoline (EEDQ), N-isobutoxycarbonyl-2-isobutoxy-1,2-dihydroquinoline (IIDQ), N-isobutoxycarbonyl-2-methoxy-1,2-dihydroquinoline (IMDQ), N-isobutoxycarbonyl-2-ethoxy-1,2-dihydroquinoline (IEDQ). As examples of mixed anhydrides, there can be mentioned chloroformates and more particularly isobutylchloroformate (IBC). The activator used is preferably N-(3-dimethylaminopropyl)-N'-ethyl carbodiimide hydrochloride.

The cross-linked copolymers according to the invention can be used, for example, in the pharmaceutical, cosmetic, biomedical, veterinary, chemical, agro-chemical or agro-alimentary fields.

A more particular subject of the invention is a pharmaceutical composition containing at least one active ingredient and, as an inert support or an excipient, at least one cross-linked copolymer according to the invention. The expression active ingredient designates any substance or mixture of substances having a therapeutic activity.

Such a composition can be produced from these different components by any standard technique known to a person skilled in the art. It can be presented, for example, in the form of matrix tablets, tablets coated with the copolymers of the present invention, multi-layered tablets, matrix pellets, pellets or microparticles coated with the copolymers of the present invention. These microparticles and pellets may or may not be contained in capsules. It can also be presented in the form of microparticles or nanoparticles at least one constituent of which is a copolymer of the present invention or else in any other form allowing oral administration. It can also be presented in any other form suited to the chosen or appropriate administration method such as suppositories or preparations for local application or injection. The quantity of active ingredient allowing effective pharmacological action, in particular therapeutic action, can vary according to the type of active ingredient, the age and/or the illness of the patient to be treated.

A subject of the present invention is also the use of a pharmaceutical composition according to the invention for a sustained release of the active ingredient(s) it contains.

Such compositions can also possess other characteristics which optionally depend on the characteristics of the initial polycarboxylic polymers such as biointegration. Thus, a pharmaceutical composition according to the invention can also be used as a bioadhesive pharmaceutical system. A subject of the present invention is therefore also the use of a pharmaceutical composition according to the invention as a biointegration system.

Compositions as defined above in which the polycarboxylic polysaccharide can be degraded by the flora of the colon can also be used as a specific release system at the level of the colon by the action of the microbial flora. The concept of specific release at the level of the colon by the action of microbial flora is based on the property of the colon to possess a very abundant microbial flora which, moreover, has the potential to metabolize substances which are slightly degraded or not degraded by the upper part of the digestive tube. Such compositions are particularly suited to conveying active ingredients intended for the treatment of diseases of the colon, which allows their effectiveness to be increased and their side effects to be reduced. These active ingredients include steroids such as dexamethasone and hydrocortisone, non-steroid anti-inflammatories such as 5-aminosalicylic acid, antineoplastics such as methotrexate, tamoxifen, antispasmodics and chemotherapy agents. Such compositions are also particularly suited for conveying active ingredients which are absorbed more efficiently at the level of the colon such as steroids or xanthine. Their direct administration at the level of the colon allows their effectiveness to be increased. Such compositions are also particularly suited to conveying active ingredients which are degraded in the upper parts of the digestive tube. Among these active ingredients, there can be mentioned peptides and proteins such as oral vaccines, insulin, contraceptive peptides, plasminogen activator peptides, growth peptides, LH/RH.

The following examples are presented in order to illustrate the above procedures and should in no event be considered as a restriction to the scope of the invention.

EXPERIMENTAL PART

EXAMPLE 1

Figure 1:
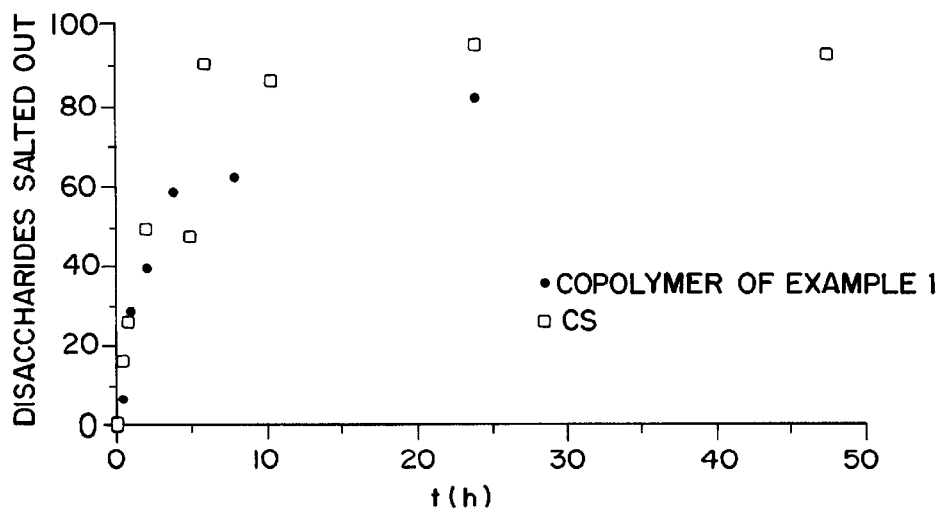
FIG. 1—Graph of the kinetics of the appearance in solution of the disaccharides originating from the degradation of the non cross-linked CS and the copolymer obtained in Example 1.

1.33 g of the sodium salt of chondroitin sulphate (A at 70%, C at 30% to) (CS), 0.29 g of the sodium salt of polymethacrylic acid (PMA) and 3.35 g of L-lysine monohydrochloride are mixed together in 9 ml of bidistilled water until a limpid solution is obtained which is subsequently degassed. Then 4.59 g of N-ethyl-N'-(3-dimethylaminopropyl) carbodiimide hydrochloride (EDC) is added. The pH is maintained between 6 and 7 by successively adding 2.5 N hydrochloric acid. The reaction is carried out at ambient temperature for 6 hours. Then the reaction medium is transferred to a dialysis apparatus (Spectra/por, cut-off threshold 12–14 KD) and dialysed 4 times against 4 liters of water each time. The precipitate obtained in this way is washed with water then dried. The sought chondroitin sulphate and polymethacrylic acid copolymer is obtained with the mass or yield of the obtained copolymer has an average of 1.53±0.12 g. The use of sulphur as a marker for chondroitin sulphate allows the definition by elementary analysis of the percentage by mass of chondroitin sulphate in the copolymer which is equal to 59±2%.

EXAMPLE 2

The operation is carried out in the same manner as in Example 1, but using 1.77 g of L-lysine monohydrochloride and 2.76 g of EDC. The mass of the copolymer obtained is 1.06±0.15 g; the percentage by mass of CS in the precipitate is 55±2.

EXAMPLE 3

The operation is carried out in the same manner as in Example 1, but using 7.06 g of L-lysine monohydrochloride and 8.21 g of EDC. The mass of the copolymer obtained is 1.61±0.12 g; the percentage by mass of CS in the precipitate is 61±1.

EXAMPLE 4

The operation is carried out in the same manner as in Example 1, but using 3 g of histidine instead of L-Lysine. The mass of the copolymer obtained is 1.94±0.01 g; the percentage by mass of CS in the precipitate is 48±3.

EXAMPLE 5

The operation is carried out in the same manner as in Example 1, but using 0.43 g of PMA, 4.5 g of L-lysine monohydrochloride and 5.82 g of EDC. The mass of the copolymer obtained is 1.86±0.05 g; the percentage by mass of CS in the precipitate is 58±2.

EXAMPLE 6

The operation is carried out in the same manner as in Example 1, but using 0.58 g of PMA, 5.45 g of L-lysine monohydrochloride and 7.05 g of EDC. The mass of the copolymer obtained is 2.07±0.01 g; the percentage by mass of CS in the precipitate is 54±2.

EXAMPLE 7

Tests on the solubilization of the copolymer of Example 1 are carried out in the following solvents and mixtures of solvents: water at pH 3 and 7, acetonitrile, ethanol, tetrahydrofuran, dichloromethane, dimethylsulphoxide, dimethylacetamide, acetone, dioxane, triethylamine, chloroform, petroleum ether, hexane, dimethylformamide, benzyl alochol, heptane, isopropyl alcohol, 1,2-propanediol, water/acetone mixture (50%/50%), water/ethanol mixture (50%/50%).

The copolymer is insoluble in all these solvents, which demonstrates its cross-linked character.

Study of the Enzymatic Degradation of Copolymers 1-spectroscopic study

We are here studying the degradation of the copolymers of the invention based on chondroitin sulphate by chondroitinases, enzymes of the microbial flora of the colon.

Suspensions of the copolymers of Examples 1 to 6, in a buffer (acetate/tris/albumin) at pH 7.3, are prepared and agitated for a few hours in order to stablize them. The suspensions contain 67 mg of CS/ml of buffer. A solution of chondroitinases is added at a rate of $3.10^{-3}$ EU (Enzymatic Unit) for each mg of CS contained in the suspension. The mixture is incubated at 37° C. At determined times, a suspension is centrifuged at 4° C. then filtered. A study of the UV absorbance of the supernatant is carried out. The disaccharides originating from the degradation of the CS have a maximum absorption at 230–240 nm (Yamagata, T. et al., *J. Biol. Chem.*, 243(7): 1523–1535(1968); Salyers, A. et al., *J. Bacteriol.*, 143(2): 772–780)). The control is a solution of non cross-linked CS prepared under the same operating conditions as above.

The kinetics of the appearance in solution of the disaccharides originating from the degradation of the non cross-linked CS and the copolymer obtained in Example 1 are shown in FIG. 1 below.

These results show that the copolymer of Example 1 is degraded by the enzymes. Comparison of the degradation of the copolymer of Example 1 with that of the control shows that the copolymer, although cross-linked, is rapidly degraded by the enzymes.

The same tests are carried out on the copolymers of Examples 2 to 6; the results show that these copolymers containing the CS are degraded by the chondroitinases.

2-rheological Study

The enzymatic degradation of the copolymers leads to the appearance of molecular chains of smaller sizes and should therefore lead to a reduction in the viscosity of the medium in which they are suspended.

A suspension of the copolymer of Example 1 in the buffer mixture (tris/acetate/albumin) is prepared under the same operating conditions as those used in the spectroscopic study as presented above. Then, 4 ml of suspension is incubated in the cylinder of the viscometer (Haake RS100) maintained at 37° C. Measurement of the initial viscosity (h) is carried out. Then, 0.8 EU of chondroitinases dissolved in 160 ml of water are added to the suspension. The control is a suspension of the copolymer of Example 1 prepared under the operating conditions previously described, without adding any enzyme and diluted in 160 ml of water. The evolution of the viscosity is monitored over time. The experiment is carried out twice for each test.

Figure 2:
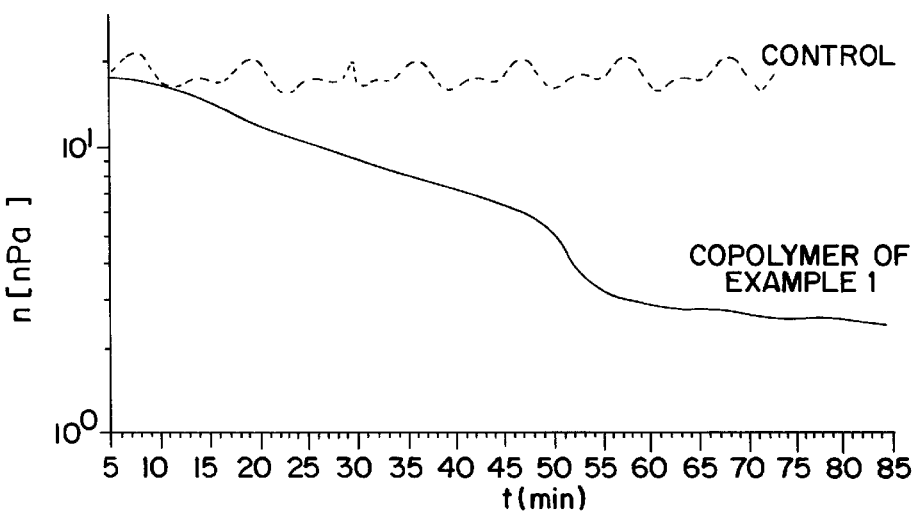
FIG. 2—A semi-log graph of the change in viscosity of the copolymer of Example 1 in the presence of enzymes (continuous lines) or in the absence of enzymes (dotted control line).

FIG. 2 is a semi-logarithmic illustration of the evolution of the viscosity of the suspension of the copolymer of Example 1 in the presence of enzymes (continuous line) or in the absence of enzymes (dotted control line). The viscosity of the control, which is of the order of 17±3 mPa.s, does not vary over time. On the other hand, in the presence of enzymes, the viscosity progressively drops from 17 mPa.s to 3 mPa.s over 55 minutes then becomes quasi-stable. This significant drop in viscosity is explained by the degradation of the copolymer by the enzymes.

Moreover, following the above spectroscopic and rheological studies carried out under the same operating conditions, there can be observed, after incubation in the presence of enzymes for 55 minutes, a virtually total drop in viscosity although only part of the disaccharides originating from the the degradation of the CS which is detected in solution. The degradation of a few sites of the copolymer by the enzymes is sufficient to entail a collapse of the three-dimensional network of the copolymer.

Study of Sustained Release Tablets

The cross-linked copolymers of Examples 1 to 6 are sieved then mixed with aminosalicylic acid (5ASA) and magnesium stearate (mass ratio 79.5/20/0.5). Then 250 mg tablets of hardness >100 N are prepared by direct compression.

Dissolution tests are carried out on the tablets prepared in this way, in a device with a rotating vane (DISSOLUTEST) at 37° C. under agitation at 50 revolutions/minute. The dissolution media used are a buffer mixture of pH 1.2 and 7.5 respectively corresponding to the artificial gastric and intestinal media (without enzymes). For each formula and in each medium, the test is carried out three times. At determined times, a sample of the dissolution medium is taken and filtered. Dosage of the 5ASA is carried out by UV spectroscopy.

Table 1 below summarizes the time (in hours) taken to release 50% of the initial dose of 5ASA ($t_{50\%}$), obtained in artificial gastric and intestinal media.

TABLE 1

| Example | $t_{50\%}$ (gastric medium) | $t_{50\%}$ (intestinal medium) |
|---|---|---|
| 1 | 2.88 | 7.66 |
| 2 | 1.42 | 1.61 |
| 3 | 6.48 | 8.29 |
| 4 | 1.22 | 1.59 |
| 5 | 7.94 | 8.65 |
| 6 | 7.96 | 11.05 |

In a gastric medium, the $t_{50\%}$'s vary from 1.2 to 8 hours thus allowing the release of the active ingredient to be modulated according to the type of copolymer. Among these copolymers, the copolymers of Examples 3, 5 and 6, respectively having $t_{50\%}$'s of 6.5, 7.9 and 8 hours, significantly moderate the release of the active ingredient.

In an intestinal medium, the $t_{50\%}$'s vary from 1.6 to 11 hours, also allowing modulation of the release of the active ingredient according to the type of copolymers. Moreover, a significant moderation of the release of the active ingredient is obtained with the copolymers of Examples 1, 3, 5 and 6. In fact, the $t_{50\%}$'s obtained with these copolymers are 7.7, 8.3, 8.7 and 11 hours respectively.

The synthesized copolymers therefore allow the creation of sustained release pharmaceutical systems according to the characteristics of the cross-linked copolymers. More particularly, those which possess the property of significantly moderating the release of the active ingredient and being degradable by chondroitinases appear to be useful candidates for creating sustained release systems at the level of the colon by action of the microbial flora.

What is claimed is:

1. A cross-linked copolymer formed by reacting at least one non-cross-linked polycarboxylic polysaccharide and at least one second non-cross-linked polycarboxylic polymer which is not a polycarboxylic polysaccharide in the presence of a cross-linking agent having at least two amine functions.

2. A pharmaceutical composition comprising an inert pharmaceutical support comprising a cross-linked copolymer of claim 1 and at least one ingredient pharmaceutically active.

3. A method of sustained release of an active pharmaceutical ingredient in warm-blooded animals comprising administering to warm-blooded animals a composition of claim 1.

4. A cross-linked copolymer of claim 1 wherein the polycarboxylic polysaccharide is selected from the group consisting of glycosaminoglycans, pectinic or alginic acid.

5. A copolymer of claim 1 wherein the polycarboxylic polysaccharide is a glycosaminoglycan selected from the group consisting of hyaluronic acid, chondroitin sulfate, heparin, dermatan sulfate and heparin sulfate and keratan sulfate.

6. A copolymer of claim 1 wherein the second polycarboxylic polymer is selected from the group consisting of polycarboxylic acrylic polymers, poly(glutamic acid), poly(aspartic acid), poly(maleic acid), poly(malic acid), and poly(fumaric acid).

7. A copolymer of claim 6 wherein the second polycarboxylic polymer is a polycarboxylic acrylic polymer.

8. A copolymer of claim 7 wherein the second polycarboxylic polymer is poly(acrylic acid) or poly(methacrylic acid).

9. A copolymer of claim 1 wherein the cross-linking agent is selected from the group consisting of diamines, polyamines and natural and synthetic amino acids.

10. A copolymer of claim 9 wherein the cross-linking agent is an amino acid selected from the group consisting of lysine, histidine and ornithine.

11. A copolymer of claim 9 wherein the cross-linking agent is a diamine selected from the group-consisting of ethylenediamine, butanediamine, hexanediamine, heptanediamine, octanediamine and dodecanediamine.

12. A copolymer of claim 9 wherein the cross-linking agent is a polyamine selected from the group consisting of chitosan, polyornithine or polylysine.

13. A copolymer of claim 1 wherein the polycarboxylic polysaccharide is degraded by flora of the colon.

14. A copolymer of claim 1 wherein the polycarboxylic polysaccharide is selected from the group consisting of chondroitin sulfate, hyaluronic acid, pectinic acid or heparin.

15. A copolymer of claim 1 wherein the polycarboxylic polysaccharide is chondroitin sulfate, the second polycarboxylic polymer is poly(acrylic acid) or poly(methacrylic acid) and the cross-linking agent is lysine or histidine.

16. A process for the preparation of a copolymer of claim 1 comprising reacting the non-crosslinked polycarboxylic polymers in an aqueous medium in the presence of the cross-linking agent and an activator.

17. The process of claim 16 wherein the activator is selected from the group consisting of a carbodiimide, a quinoline derivative and a mixed acid anhydride.

18. A pharmaceutical composition comprising an inert pharmaceutical support comprising a cross-linked copolymer of claim 13 and at least one ingredient pharmaceutically active.

19. The method of claim 3 wherein the active pharmaceutical ingredient is one to treat diseases of colon.

20. The method of claim 3 wherein the active pharmaceutical ingredient is absorbed at the colon level.

21. The method of claim 3 wherein the active pharmaceutical ingredient is degraded in the upper parts of the digestive system.

* * * * *